US009915607B2

(12) United States Patent
Kitazawa et al.

(10) Patent No.: US 9,915,607 B2
(45) Date of Patent: Mar. 13, 2018

(54) OPTICAL SENSOR SYSTEM

(71) Applicant: Sharp Kabushiki Kaisha, Osaka-shi, Osaka (JP)

(72) Inventors: Tazuko Kitazawa, Osaka (JP); Noboru Iwata, Osaka (JP); Takanobu Sato, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 0 days.

(21) Appl. No.: 14/900,330

(22) PCT Filed: Mar. 17, 2014

(86) PCT No.: PCT/JP2014/057112
§ 371 (c)(1),
(2) Date: Dec. 21, 2015

(87) PCT Pub. No.: WO2014/208144
PCT Pub. Date: Dec. 31, 2014

(65) Prior Publication Data
US 2016/0153900 A1 Jun. 2, 2016

(30) Foreign Application Priority Data
Jun. 26, 2013 (JP) .................................. 2013-134105

(51) Int. Cl.
*G01N 21/55* (2014.01)
*G01N 21/41* (2006.01)
(Continued)

(52) U.S. Cl.
CPC ........... *G01N 21/41* (2013.01); *G01N 21/554* (2013.01); *G01N 21/7746* (2013.01);
(Continued)

(58) Field of Classification Search
CPC .. G01N 21/41; G01N 21/554; G01N 21/7746; G01N 2201/06113; G01N 2201/068; G01N 2201/08
(Continued)

(56) References Cited

U.S. PATENT DOCUMENTS

2007/0196043 A1 8/2007 Peled et al.
2008/0130003 A1* 6/2008 Kuroda ................ G01N 21/554
356/445
(Continued)

FOREIGN PATENT DOCUMENTS

CN 101551329 A 10/2009
JP 2007-537439 A 12/2007
(Continued)

OTHER PUBLICATIONS

Official Communication issued in International Patent Application No. PCT/JP2014/057112, dated Jun. 3, 2014.
(Continued)

*Primary Examiner* — Sunghee Y Gray
(74) *Attorney, Agent, or Firm* — Keating & Bennett, LLP

(57) ABSTRACT

An optical sensor system includes an optical sensor head having a light-emitting device and a detector which detects light emitted from the light-emitting device, and a calculator circuit. The light-emitting device includes a resonator which includes a first reflective surface, a second reflective surface facing the first reflective surface, and a waveguide provided between the first reflective surface and the second reflective surface. At least one metal microparticle capable of exciting surface plasmon is formed on the first reflective surface. The calculator circuit calculates an environment parameter at the first reflective surface on the basis of a detected value from the detector.

6 Claims, 10 Drawing Sheets

(51) Int. Cl.
*G01N 21/552* (2014.01)
*G01N 21/77* (2006.01)

(52) U.S. Cl.
CPC .............. *G01N 2201/068* (2013.01); *G01N 2201/06113* (2013.01); *G01N 2201/08* (2013.01)

(58) Field of Classification Search
USPC ........................................ 356/445
See application file for complete search history.

(56) References Cited

U.S. PATENT DOCUMENTS

| | | |
|---|---|---|
| 2009/0244540 A1 | 10/2009 | Wang et al. |
| 2009/0251682 A1 | 10/2009 | Wang et al. |
| 2010/0157306 A1* | 6/2010 | Choi .................. G01N 21/554 356/445 |
| 2013/0259418 A1 | 10/2013 | Kontani |

FOREIGN PATENT DOCUMENTS

| | | | |
|---|---|---|---|
| JP | 2008-203133 A | 9/2008 | |
| JP | 4224641 B2 | 2/2009 | |
| JP | 2010-25580 A | 2/2010 | |
| JP | 2010-107206 A | 5/2010 | |
| JP | 2010-185738 A | 8/2010 | |
| JP | 2012-122915 A | 6/2012 | |
| JP | 2012122915 * | 6/2012 | ........... G01N 21/553 |

OTHER PUBLICATIONS

Rayford II et al., "Optical Properties of Gold Nanospheres", Nanoscape vol. 2, Issue 1, Spring 2005, pp. 27-33.
Kooij et al., "Shape and size effects in the optical properties of metallic nanorods", Physical Chemistry Chemical Physics, 8, Mar. 10, 2006, pp. 3349-3357.
Li et al, "Optical properties of Au/Ag core/shell nanoshuttles", Optics Express vol. 16, No. 18, Sep. 1, 2008, pp. 14288-14293.

* cited by examiner

OPTICAL SENSOR SYSTEM

TECHNICAL FIELD

A present invention relates to an optical sensor system utilizing surface plasmon resonance.

BACKGROUND ART

A surface plasmon sensor which detects the refractive index of a metal film surface through surface plasmon resonance (resonance of incident light with vibration of an electron in a metal microparticle) is used mainly for research purposes in the field of biotechnology because of high sensitivity and lack of the need for a marker.

A general sensing method using such a sensor condenses light via a prism to cause the light to come incident on a metal film provided on one surface of the prism and detects light reflected from the metal film, thereby analyzing the refractive index of the surface of the metal film from an angle of incidence at which the light is absorbed. Generally, an adsorption layer which adsorbs a particular molecule is provided in advance at the metal film, and the refractive index is converted into the concentration of the molecule.

However, a complicated apparatus composed of a light source, a lens, a prism, and the like is needed to perform the sensing method. The need for accuracy at the time of assembly of the apparatus, strict temperature control that prevents the apparatus from changing over time, correction of a deviation in a sensing result, and the like entails high cost and increased apparatus size. Additionally, high-accuracy detection at the molecular level is difficult for the above-described apparatus.

Aside from this, a method using a resonator is proposed for small-sized and high-sensitivity detection.

For example, Japanese Unexamined Patent Application Publication No. 2007-537439 discloses a sensor which incorporates a micro-resonator in a part of a planar waveguide and detects a change in spectral response due to a change in the refractive index of a surface of the micro-resonator. The micro-resonator is a resonator for surface plasmon waves. The micro-resonator includes a thin metal layer, and a reflecting section uses a distributed Bragg reflector (DBR) with a periodic structure.

Japanese Patent No. 04224641 discloses a localized surface plasmon sensor in which a metal microparticle layer sized to excite localized surface plasmon resonance is formed on an end face of an optical fiber, and a molecular layer of a molecule complementary to a detection target molecule is formed on a surface of the metal microparticle layer. The localized surface plasmon sensor detects the detection target molecule adsorbed or bonded to the complementary molecule using a change in light reflected or scattered from the end face of the optical fiber.

However, the sensor disclosed in Japanese Unexamined Patent Application Publication No. 2007-537439 detects a detection target by converting light from a light source into surface plasmon, causing the surface plasmon to react with the detection target with the micro-resonator resonating, and reconverting the surface plasmon into light, and loss of light intensity occurs in the conversion from light into surface plasmon. Additionally, since a resonator with a length of 2 to 10 microns is utilized, a surface plasmon wave as a damped wave is lost inside the resonator, and improvement in sensitivity cannot be expected. Moreover, there is a limit to a size reduction due to the need for a separate light source.

The sensor disclosed in Japanese Patent No. 04224641 does not use a resonator and include low sensitivity. When light from a light source is coupled to the optical fiber in the sensor, loss of light intensity occurs.

SUMMARY OF THE INVENTION

Preferred embodiments of the present invention, provide an optical sensor system which allows achievement of higher sensitivity and downsizing.

An optical sensor system according to one aspect of a preferred embodiment of the present invention includes an optical sensor head, the optical sensor head including a light-emitting device which includes a first reflective surface, a second reflective surface facing the first reflective surface, and a waveguide provided between the first reflective surface and the second reflective surface and a detector which detects light emitted from the light-emitting device and including at least one metal microparticle formed on the first reflective surface which excites surface plasmon, and a calculator circuit which calculates an environmental parameter at the first reflective surface on a basis of a detected value from the detector.

In the one aspect of a preferred embodiment of the present invention, the first reflective surface, the second reflective surface, and the waveguide constitute a resonator. The environmental parameter at the first reflective surface changes, and an excitation wavelength for surface plasmon excited by the metal microparticle changes, which causes a change in reflectivity of the first reflective surface. The change changes an oscillation condition for the light-emitting device, and intensity of light emitted from the light-emitting device changes. Thus, the environmental parameter at the first reflective surface 4 can be detected on the basis of the intensity of the light emitted from the light-emitting device detected by the detector and a parameter related to the oscillation condition, into which the intensity is converted.

Note that the environmental parameter is an indicator of a factor that causes a change in optical properties (a change in the refractive index of surroundings of the metal microparticle or the metal microparticle itself or a change in reflectivity of the first reflective surface) at the first reflective surface.

Since a change in intensity due to a change in the oscillation condition is detected, higher sensitivity can be achieved than in a case where a change in intensity due to a change in the excitation wavelength for the surface plasmon is simply detected.

Additionally, at least one metal microparticle capable of surface plasmon excitation is formed on the first reflective surface of the light-emitting device. Thus, the optical sensor head is constructed so as to be about the same size as the light-emitting device, which allows a large size reduction.

The above and other elements, features, steps, characteristics and advantages of the present invention will become more apparent from the following detailed description of the preferred embodiments with reference to the attached drawings.

DESCRIPTION OF PREFERRED EMBODIMENTS

First Preferred Embodiment

An optical sensor head 1 in an optical sensor system according to a first preferred embodiment of the present invention will be described with reference to FIGS. 1 to 4 as follows.

Figure 1:
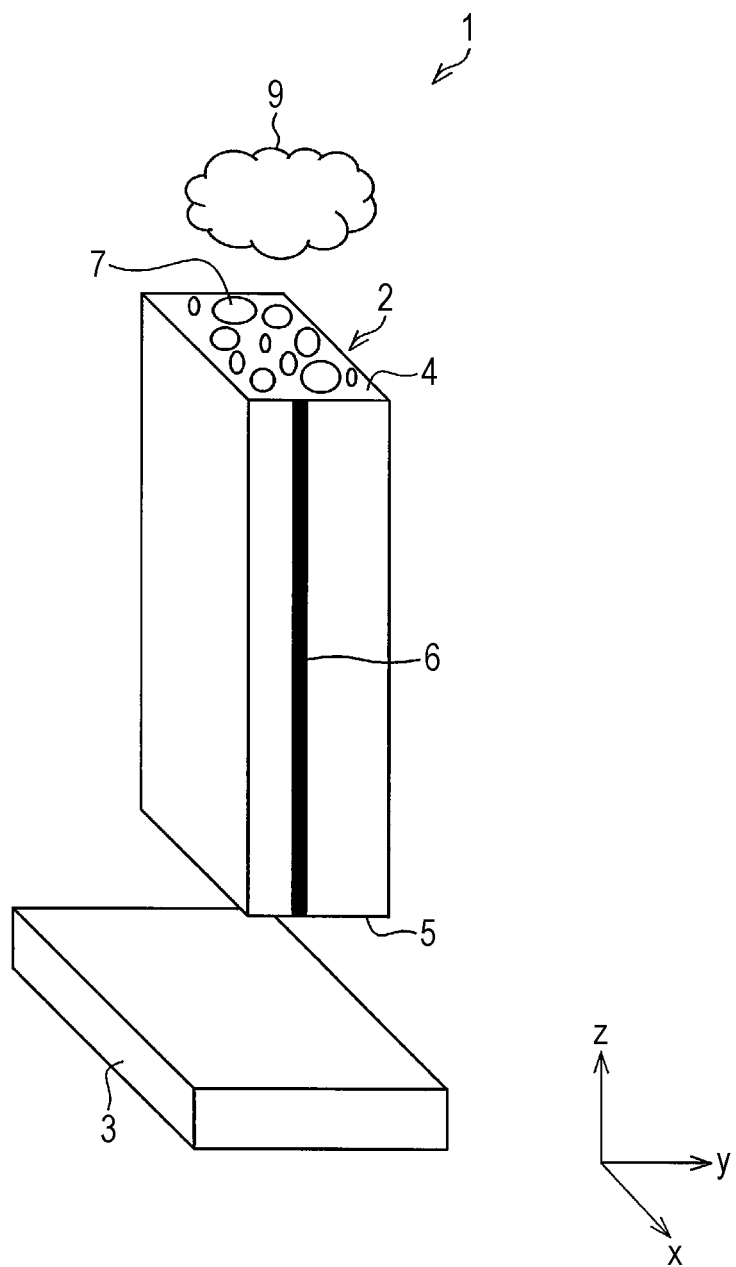
FIG. 1 is a perspective view showing an example of the configuration of an optical sensor head in an optical sensor system according to a first preferred embodiment of the present invention.
Figure 2:
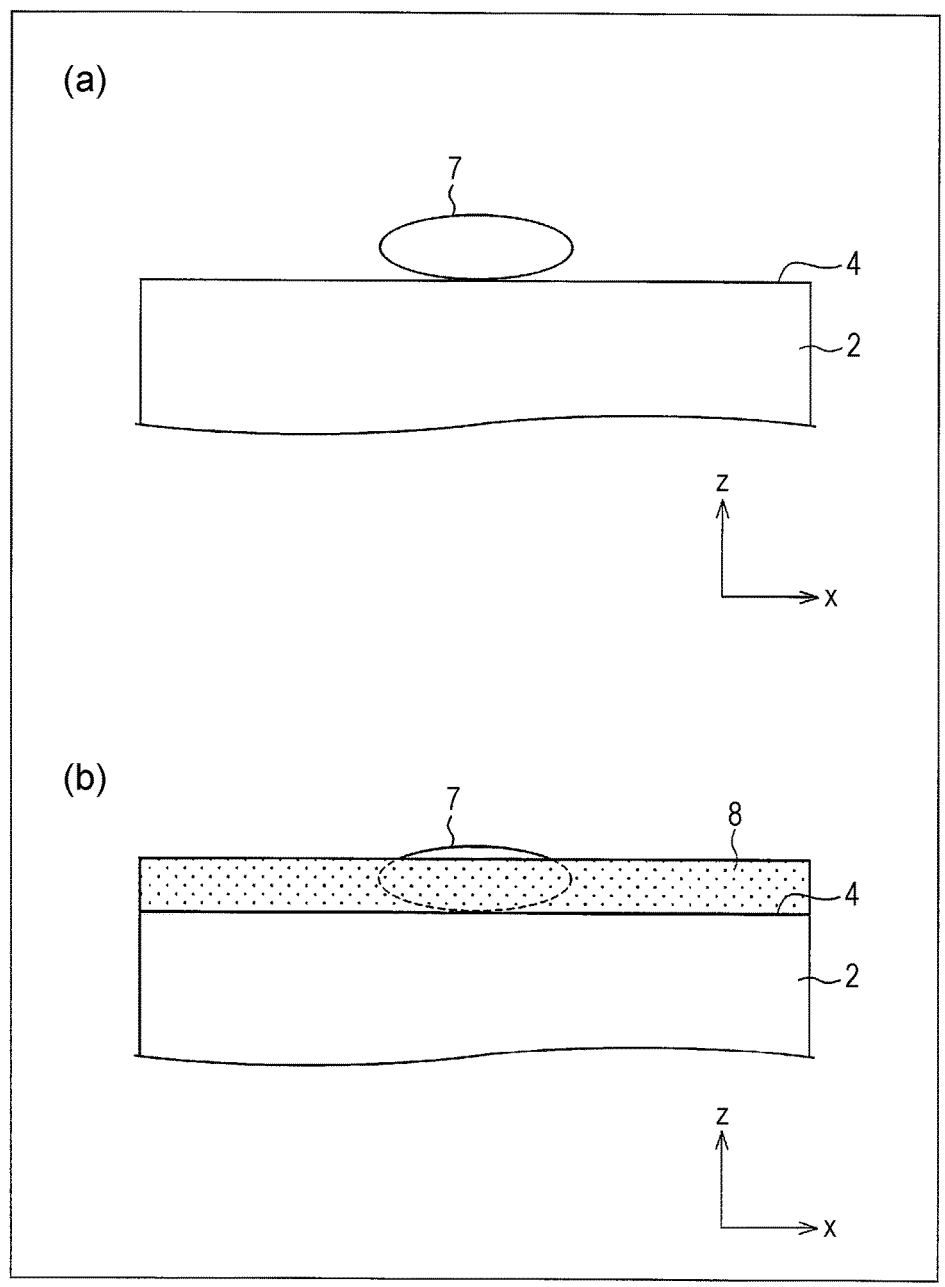
FIG. 2(a) is a cross-sectional view showing the arrangement of a metal microparticle in the optical sensor head.
FIG. 2(b) is a cross-sectional view showing the arrangement of the metal microparticle with an intervening protective layer in the optical sensor head.
Figure 3:
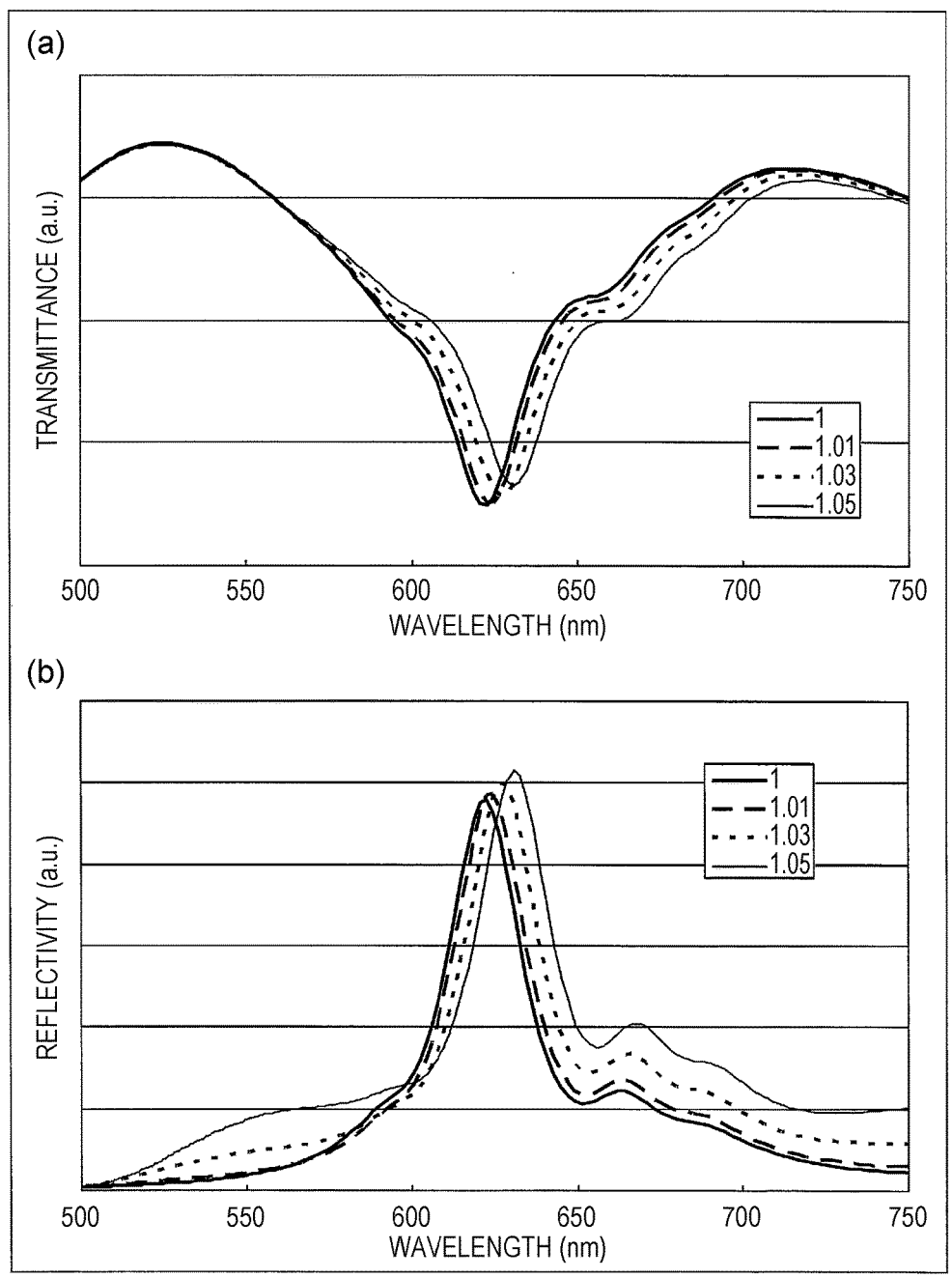
FIG. 3(a) is a graph showing a relation between a surface plasmon excitation wavelength in the optical sensor head and light transmittance of the metal microparticle.
FIG. 3(b) is a graph showing a relation between the surface plasmon excitation wavelength in the optical sensor head and light reflectivity of the metal microparticle.

FIG. 1 is a perspective view showing an example of the configuration of the optical sensor head 1 in the optical sensor system according to the present preferred embodiment.

As shown in FIG. 1, the optical sensor head 1 includes a light-emitting device 2, a metal microparticle 7, and a detector 3. Although not shown, the components are integrally packaged. The light-emitting device 2 is formed in the shape of a rectangular parallelepiped and includes a first reflective surface 4, a second reflective surface 5 which faces the first reflective surface 4, and a waveguide 6 which is provided between the first reflective surface 4 and the second reflective surface 5. The metal microparticle 7 is formed on the first reflective surface 4.

In the light-emitting device 2, the first reflective surface 4 and the second reflective surface 5 are provided at two ends of the waveguide 6. The light-emitting device 2 includes a structure that causes light to travel through the waveguide 6 between the first reflective surface 4 and the second reflective surface 5 alternately in a z direction and a direction opposite to the z direction. Since the waveguide 6 has a gain, light traveling back and forth through the waveguide 6 is amplified by the gain, and part of the light is radiated from the first reflective surface 4 and the second reflective surface 5 to the outside. As a preferred embodiment of the present invention, the light-emitting device 2 includes the first reflective surface 4, the second reflective surface 5, and the waveguide 6 to thereby constitute a resonator.

As a specific example of the light-emitting device 2, a commercially-available laser device may be used. For a size reduction, a semiconductor laser device is particularly preferable. A distributed feedback laser device may also be used to increase sensitivity. As will be described later, use of a semiconductor laser device allows easy calculation of an environmental parameter at the first reflective surface 4 from the intensity of light radiated to the outside through at least either one of the first reflective surface 4 and the second reflective surface 5 detected by the detector 3.

Note that the environmental parameter will be described in detail later.

If a laser is used as the light-emitting device 2, either multi-mode oscillation or single-mode oscillation will do. Generally, multi-mode oscillation is higher in intensity than single-mode oscillation, and single-mode oscillation is narrower in an oscillation spectrum of the light-emitting device 2 than multi-mode oscillation. Thus, use of single-mode oscillation leads to higher detection resolution for a surface plasmon excitation wavelength range and higher detection sensitivity.

A commercially-available laser device (for example, a semiconductor laser) is already provided with the first reflective surface 4, the second reflective surface 5, and the waveguide 6. However, it is also possible to form other films on the first reflective surface 4 and the second reflective surface 5 to adjust their reflectivity.

The detector 3 may be a commercially-available photodetector or a spectroscope, for example, or other suitable device. The commercially-available photodetector can detect light intensity alone but is small in size and low in cost. The spectroscope cannot be made as small as the photodetector but can detect a reflection spectrum. The spectroscope can obtain not only light intensity but also a piece of information on a wavelength shift. Detection surfaces of the detectors are able to be slightly tilted such that light to be detected does not reflect and return to a light source.

The detector 3 is able to be installed at any location as long as the detector 3 can detect light emitted from the light-emitting device 2, that is, light having passed through the first reflective surface 4 or the second reflective surface 5 of the light-emitting device 2.

In the case of a commercially-available semiconductor laser, a photoelectric detector (for example, a photodiode) which monitors the intensity of light emitted from the semiconductor laser is provided inside to keep optical output of the semiconductor laser constant. If a commercially-available semiconductor laser is adopted as the light-emitting device 2, such a photoelectric detector is able to be utilized as the detector 3. This allows easy fabrication of the optical sensor head 1.

The metal microparticle 7 is made of a metal which excites surface plasmon. More specifically, a material, such as gold, silver, or aluminum, is mainly utilized as the metal microparticle 7.

At the metal microparticle 7, surface plasmon is excited by light emitted from the light-emitting device 2. A surface plasmon excitation wavelength range for excitation of surface plasmon at the metal microparticle 7 changes due to an environmental change. The environmental change may be a change of temperature, humidity, or pressure, or a change in the refractive index of surroundings of the metal microparticle 7 or the metal microparticle 7 itself due to the presence of a detection target 9 in the surroundings of the metal microparticle 7. The detection target 9 may be arranged alone in the surroundings of the metal microparticle 7 or may be arranged in the surroundings of the metal microparticle 7 while being contained in gas (for example, air) or liquid (for example, water).

It suffices that, at the metal microparticle 7, surface plasmon be excited at the wavelength of light emitted from the light-emitting device 2. The shape of the metal microparticle 7 is thus not limited to a particular shape, such as a spherical shape, joined spheres, an oval sphere, a rod shape, a prism, a maze-like shape, or a star shape.

Note that the shape of the metal microparticle 7 affects excitation of surface plasmon. For example, as disclosed in Cleveland Eugene Rayford II, George Schatz and Kevin Shuford, "Optical Properties of Gold Nanospheres", Nanoscape Volume. 2, Issue 1, p.p. 27-33 (Spring 2005), it is known that, if the size becomes not less than 100 nm, a peak of an excitation wavelength shifts to the long-wavelength side, and the width increases.

Even if the metal microparticle 7 includes a shape with an aspect ratio other than 1, such as joined spheres, an oval sphere, a rod shape, or a maze-like shape, the excitation wavelength changes. The aspect ratio of the metal microparticle 7 will be described with reference to FIG. 2.

FIG. 2(a) is a cross-sectional view showing the arrangement of a metal microparticle in the optical sensor head 1, and FIG. 2(b) is a cross-sectional view showing the arrangement of a metal microparticle with an intervening protective layer in the optical sensor head 1.

In the configuration shown in FIG. 2(a), a length in an x direction of the metal microparticle 7 is three times a length in the z direction. Assume that a length in a y direction of the metal microparticle 7 is equal to that in the x direction. If the metal microparticle 7 is an oval sphere, as a preferred embodiment of the present invention, the aspect ratio of the x direction and the y direction to the z direction of the metal microparticle 7 is 3.

The excitation wavelength increases with an increase in an aspect ratio of a polarization direction of the light-emitting device 2 over a configuration in which the metal microparticle 7 includes a spherical shape (an aspect ratio of 1). More specifically, if the metal microparticle 7 includes a spherical shape with a diameter not more than 100 nm in the air, the surface plasmon excitation wavelength is around 510 nm when the material for the metal microparticle 7 is Au and is around 360 nm when the material is Ag.

However, if the material is Au, and the aspect ratio of the polarization direction of the light-emitting device 2 is 2, the surface plasmon excitation wavelength is around 590 nm, as disclosed in E. Stefan Kooij and Bene Poelsema, "Shape and size effects in the optical properties of metallic nanorods", Physical Chemistry Chemical Physics, 2006, 8, p.p. 3349-3357 (published on Mar. 10, 2006). It is known that the surface plasmon excitation wavelength shifts to the long-wavelength side with an increase in aspect ratio, as described above.

In the configuration shown in FIG. 2(b), a part of the metal microparticle 7 is covered with a protective layer 8. The protective layer 8 is preferably formed of a material which includes no absorption at an emission wavelength of the light-emitting device 2 and exhibits transparency. As the material, a dielectric, such as $SiO_2$, is generally used.

The configuration, in which a part of the metal microparticle 7 is covered with the protective layer 8, prevents the metal microparticle 7 from changing over time due to the detection target 9 or any other substance. Since the refractive index of the surroundings of the metal microparticle 7 is changed by the protective layer 8, the surface plasmon excitation wavelength changes. For this reason, the refractive index of the surroundings of the metal microparticle 7 can be increased with the protective layer 8. The surface plasmon excitation wavelength range can thus be adjusted with respect to the emission wavelength of the light-emitting device 2.

Note that if surface plasmon excited by the metal microparticle 7 is present outside the protective layer 8, a change in an environmental parameter outside the protective layer 8 changes pump intensity for surface plasmon. Along with this, the reflectivity at at least either one of the first reflective surface 4 with the metal microparticles 7 formed thereon and the second reflective surface 5 changes. With this change, an oscillation condition inside the light-emitting device 2 changes, and the above-described reflectivity is detected as a change in the intensity or wavelength of light radiated from at least either one of the first reflective surface 4 and the second reflective surface 5, which allows detection of a change in environmental parameter in a portion where surface plasmon is present. For this reason, the protective layer 8 is able to cover the whole of the metal microparticle 7. This configuration can enhance the effect of the protective layer 8 of preventing the metal microparticle 7 from changing over time. Additionally, since a surface area by which the protective layer 8 covers the metal microparticle 7 increases, a refractive index in the surroundings of the metal microparticle 7 can be made higher with the protective layer 8. It is thus possible to adjust the surface plasmon excitation wavelength range to be longer wavelength with respect to the emission wavelength of the light-emitting device 2.

On the other hand, if surface plasmon is absent outside the protective layer 8, the pump intensity for surface plasmon does not change (or changes very slightly) even when the environmental parameter outside the protective layer 8 changes. The oscillation condition inside the light-emitting device 2 makes no change. For this reason, the intensity or wavelength of light emitted from at least either one of the first reflective surface 4 and the second reflective surface 5 does not change, and a change in environmental parameter cannot be detected.

Although it suffices if one or more metal microparticles 7 are formed on the first reflective surface 4, a plurality of metal microparticles 7 are preferably formed within a range irradiated with light from the light-emitting device 2. In this case, the plurality of metal microparticles 7 is able to be different in size and aspect ratio from each other.

The operation of the optical sensor head 1 with the above-described configuration will be described.

The aforementioned change in the environmental parameter at the first reflective surface 4 changes the refractive index of the surroundings of the metal microparticle 7 or the metal microparticle 7 itself, which causes a change in the surface plasmon excitation wavelength at the metal microparticle 7. When the reflectivity at the metal microparticle 7, that is, the first reflective surface 4 changes due to the change, the change in reflectivity affects the resonator of the light-emitting device 2, which results in a change in the oscillation condition for the light-emitting device 2.

A change in the oscillation condition is detected as a change in the intensity or wavelength of light emitted from at least either one of the first reflective surface 4 and the second reflective surface 5, and such changes are converted into a change in the environmental parameter. In the present application, the environmental parameter is an indicator of a factor that causes a change in optical properties (a change in the refractive index of the surroundings of the metal microparticle 7 or the metal microparticle 7 itself or a change in the reflectivity of the first reflective surface 4) at the first reflective surface 4. More specifically, examples of the environmental parameter include temperature, humidity, and pressure, oxidation and reduction power, and the types, concentrations, and quantities of a gas, a liquid, and a solid (the detection target 9) present in the surroundings of the metal microparticle 7.

If the light-emitting device 2 is a semiconductor laser device, a change in at least either one of differential efficiency and a threshold current is able to be detected.

Note that, in the present preferred embodiment, a refractive index subsumes a complex refractive index. That is, the same applies to a case where an extinction coefficient changes.

A specific operation of the optical sensor head 1 will be described below using a result of a finite difference time domain (FDTD) simulation and theoretical calculation.

FIG. 3(a) is a graph showing a relation between the surface plasmon excitation wavelength in the optical sensor head 1 and the light transmittance of the metal microparticle 7. FIG. 3(b) is a graph showing a relation between the surface plasmon excitation wavelength in the optical sensor head 1 and the light reflectivity of the metal microparticle 7. FIGS. 3(a) and 3(b) show results of calculating the above-described relations by FDTD simulations.

The above-described FDTD simulations each assume the metal microparticle 7 that is made of Au and includes the shape of a prism including a minor axis of 20 nm, a major axis of 60 nm, and an aspect ratio of 3. A polarization direction of incident light is a major axis direction of the metal microparticle 7. FIGS. 3(a) and 3(b) both assume a state where the metal microparticle 7 is in the air and show a case where the refractive index in the surroundings of the metal microparticle 7 is 1.0 and increases to 1.01, 1.03, and 1.05 due to the presence of the detection target 9 in the surroundings of the metal microparticle 7, for example.

As can be seen from FIGS. 3(a) and 3(b), the surface plasmon excitation wavelength varies to a given degree around a peak wavelength. For example, the range of the surface plasmon excitation wavelength can be obtained by calculating differences in transmittance and reflectivity between a configuration with the metal microparticle 7 and a configuration without the metal microparticle 7. The same applies to a case where the range is wide due to non-uniformity of the metal microparticles 7 in size, aspect ratio, and alignment.

In the present preferred embodiment, the range of the surface plasmon excitation wavelength will be referred to as a surface plasmon excitation wavelength range hereinafter. The surface plasmon excitation wavelength range can be identified by, for example, measuring from the outside the reflectivity of the first reflective surface 4 in a portion with the metal microparticle 7 formed therein and the reflectivity of the first reflective surface 4 in a portion with no metal microparticle 7 formed therein and obtaining the difference between the reflectivities. In the identification of the surface plasmon excitation wavelength range, the measured reflectivities are able to be corrected, as needed.

As shown in FIG. 3(a), if the refractive index is 1.0, the transmittance is low at the surface plasmon excitation wavelength of 623 nm, for example. This shows that light is absorbed by surface plasmon resonance at the metal microparticle 7. As shown in FIG. 3(b), if the refractive index is 1.0, the reflectivity is high. This is because there is little reflection at the metal microparticle 7, and only scattered light returns. As the refractive index increases to 1.01, then to 1.03, and then to 1.05, for example, the surface plasmon excitation wavelength range shifts. Thus, the peak wavelength with a lowest transmittance and a highest reflectivity shifts sequentially to 625 nm, then to 627 nm, and then to 631 nm, for example.

If the emission wavelength of the light-emitting device 2 is fixed, a change in the refractive index in the surroundings of the metal microparticle 7 increases the transmittance of the metal microparticle 7 and decreases the reflectivity. On the same principle, the peak wavelength also shifts when the refractive index of the metal microparticle 7 itself changes.

A non-limiting example of a method for manufacturing the optical sensor head 1 shown in FIG. 1 will be described.

As the light-emitting device 2, a commercially-available laser device is able to be used. The metal microparticle 7 is able to be formed at the first reflective surface 4 of the commercially-available laser device. A commercially-available photodetector is able to be installed as the detector 3 such that light emitted to the outside through the second reflective surface 5 can be detected.

For example, if a semiconductor laser device is used as the light-emitting device 2, a package, into which a semiconductor laser device and a photodetector which monitors emission intensity from a back surface of the semiconductor laser element are combined, can be used. If a film of the material for the metal microparticle 7 is formed to a thickness of several nm on an exit surface (the first reflective surface 4) of the semiconductor laser device by sputtering, deposition, or the like such that a p electrode and an n electrode are not electrically continuous, the material grows like islands, and the maze-like metal microparticles 7 can be formed. At this time, a plurality of metal microparticles 7 are formed and vary in size and aspect ratio.

As disclosed in M. Li, Z. S. Zhang, X. Zhang, K. Y. Li and X. F. Yu, "Optical properties of Au/Ag core/shell nanoshuttles", Optics Express Vol. 16, No. 18, p.p. 14288-14293 (published on Aug. 28, 2008), it is also possible to form the metal microparticle 7 in a spherical shape, an oval sphere, a rod-like shape, or the like on the first reflective surface 4 through chemical synthesis. In this case, even if a plurality of metal microparticles 7 are formed, the metal microparticles 7 can be made almost uniform such that the metal microparticles 7 vary little in size and aspect ratio.

A modification of the optical sensor head 1 will now be described.

If the light-emitting device 2 is utilized in gas, sensing is possible only with the above-described configuration. However, for more accurate measurement or utilization in liquid, ingenuity is needed. In particular, if the light-emitting device 2 is a semiconductor laser device, when the optical sensor head 1 is brought into direct contact with liquid, a p electrode and an n electrode become electrically continuous in the semiconductor laser device. The light-emitting device 2 ceases to emit light and may be broken.

Figure 4:
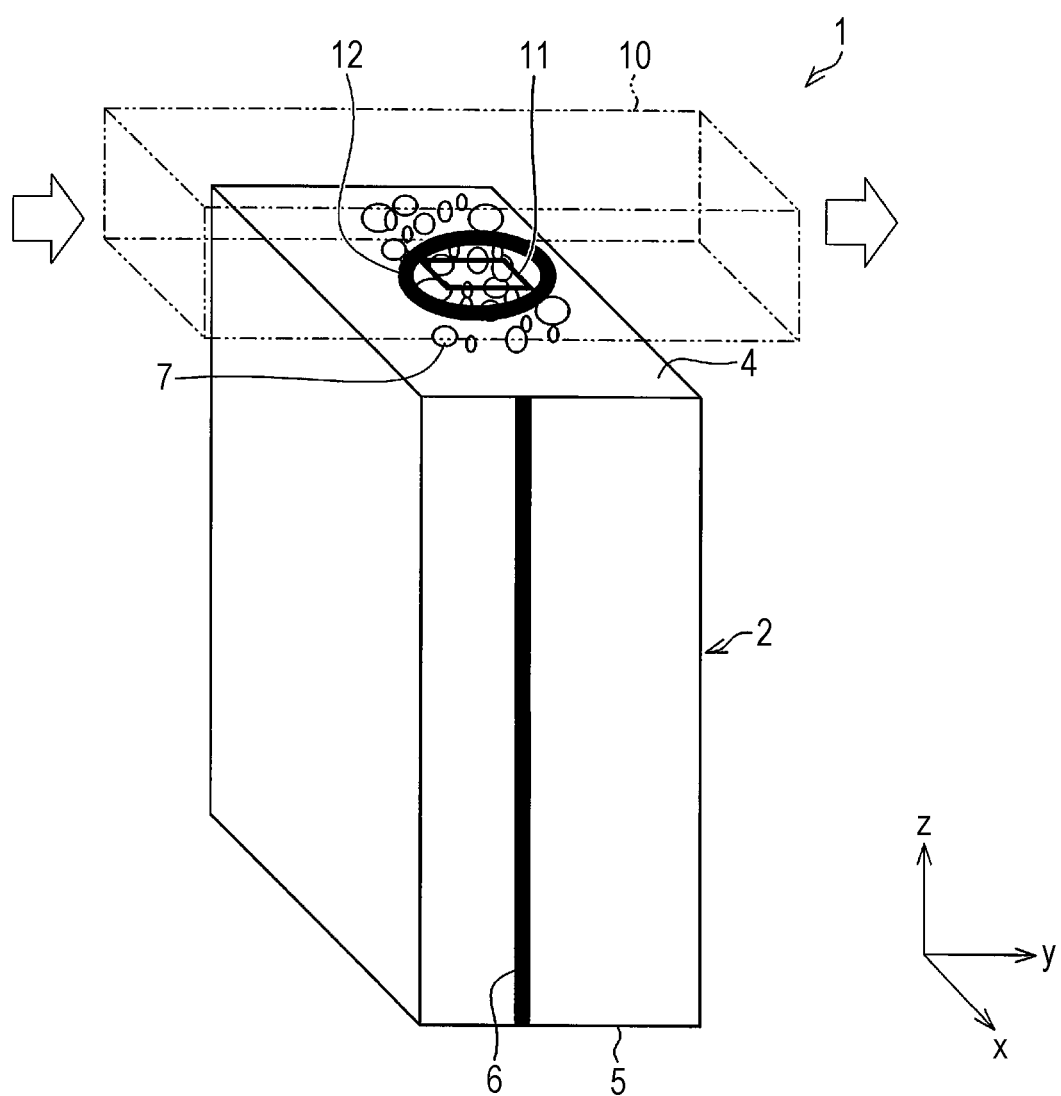
FIG. 4 is a perspective view of the optical sensor head according to a modification of the first preferred embodiment of the present invention.
Figure 5:
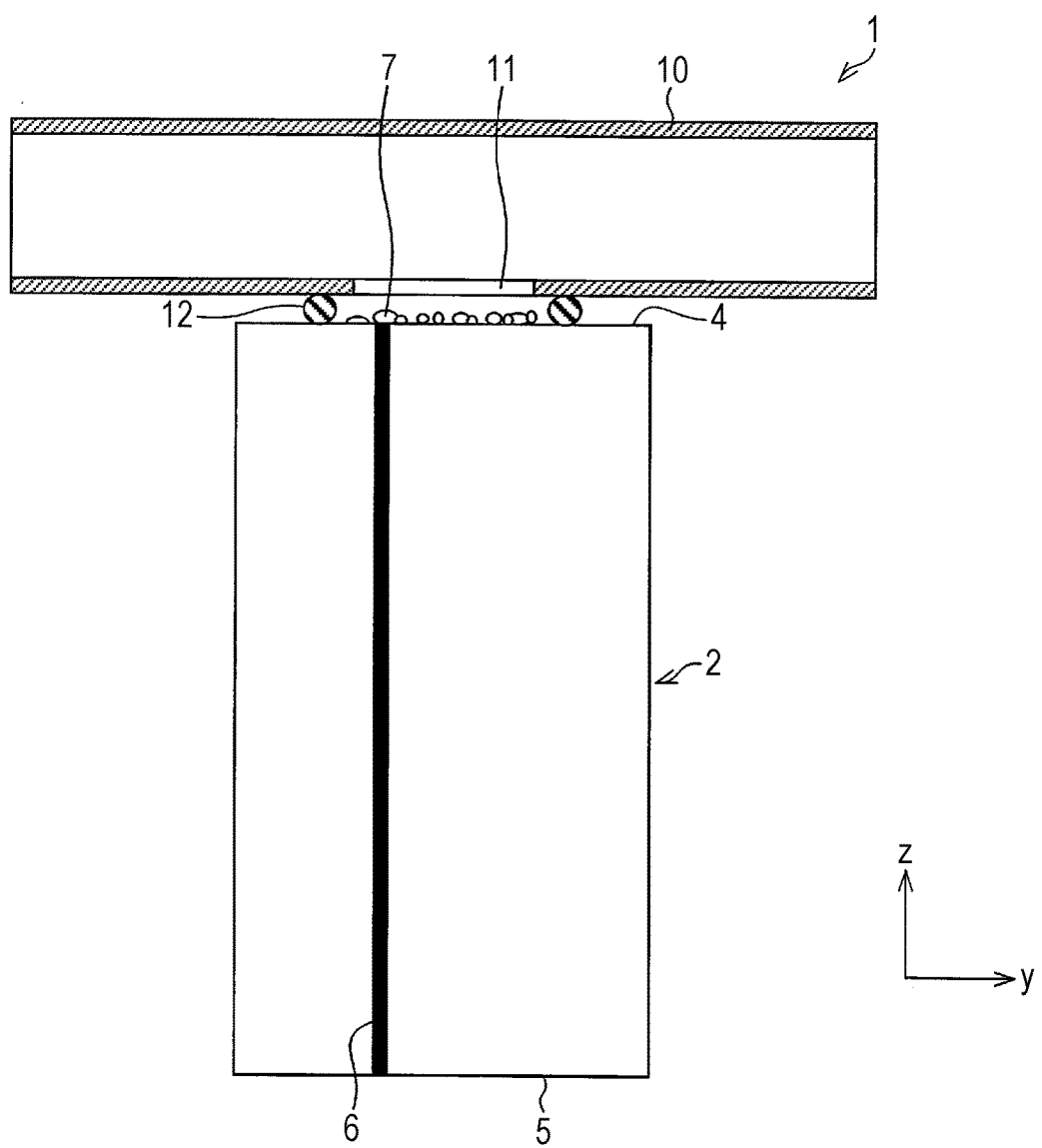
FIG. 5 is a side view of the optical sensor head according to the modification.

To avoid the above-described inconvenience, it is preferable to use a member which lets at least either one of gas and liquid containing the detection target 9 flow only near an end of the waveguide 6 at the first reflective surface 4. FIG. 4 is a perspective view showing an example of the optical sensor head 1 according to the modification including a flow-path member 10 which is the above-described member. FIG. 5 is a side view of the optical sensor head 1 according to the modification.

As shown in FIGS. 4 and 5, the optical sensor head 1 according to the present modification includes the flow-path member 10, in addition to the light-emitting device 2. The flow-path member 10 is formed in the shape of a square tube and includes in its inside a flow path for letting the detection target 9 flow from left to right in FIGS. 4 and 5. A window 11 (an opening portion) is provided in a central portion at a lower surface of the flow-path member 10. The window 11 is squarely open to expose the flow path to the first reflective surface 4 side.

Note that the flow-path member 10 is not limited to the shape of a square tube and is able to be formed in any other shape. The window 11 is also not limited to a square shape and is able to be formed in any other shape.

An O-ring 12 is provided between the first reflective surface 4 and the flow-path member 10. The O-ring 12 is arranged such that a whole open region of the window 11 and an emission range of the first reflective surface 4 fit inside the O-ring 12. The O-ring 12 is in close contact in the z direction with the first reflective surface 4 and the flow-path member 10.

The emission range is an area by which light radiated from the light-emitting device 2 can detect the detection target 9 at the first reflective surface 4. If the window 11 is formed and installed so as to face only a part of the emission range, a portion not facing the window 11 of the emission range does not contribute to detection, which invites a reduction in detection sensitivity. A region in the surroundings of the window 11 in the flow-path member 10 is made to be in close contact with the first reflective surface 4 via the O-ring 12 such that at least either one of gas and liquid containing the detection target 9 does not leak out.

The optical sensor head 1 provided with the above-described flow-path member 10 can let gas or liquid containing the detection target 9 flowing through the flow path of the flow-path member 10 flow to a desired spot without leakage.

An optical sensor system 21 according to the present preferred embodiment will be described with reference to FIGS. 6 to 10.

Figure 6:
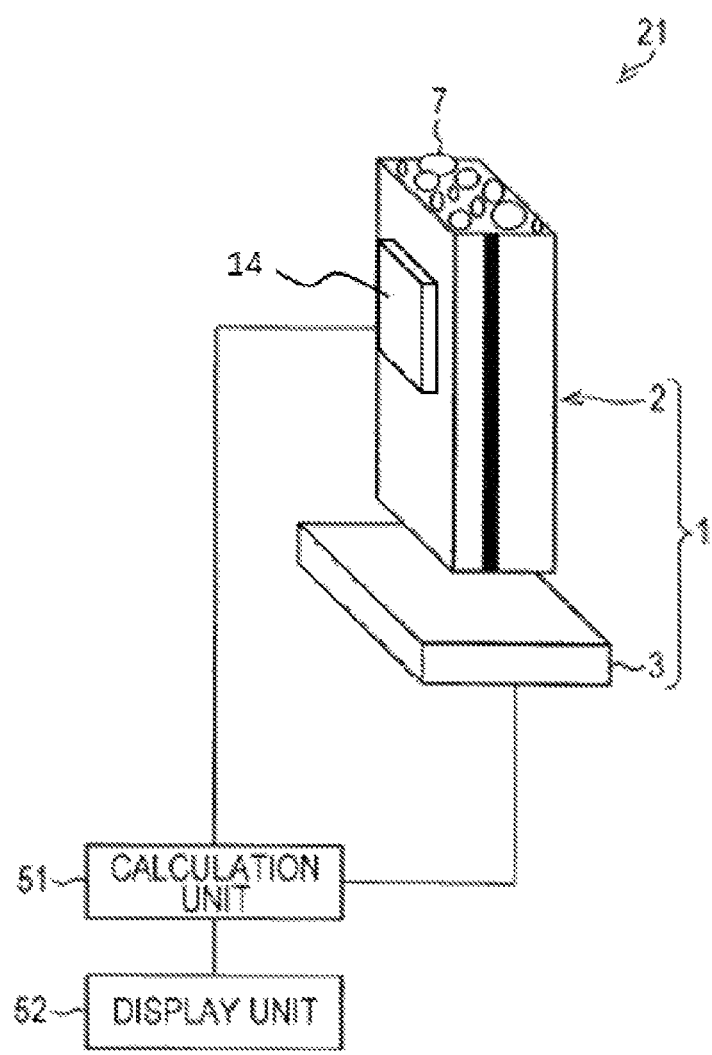
FIG. 6 is a perspective view showing an example of the configuration of the optical sensor system according to the first preferred embodiment of the present invention.
Figure 7:
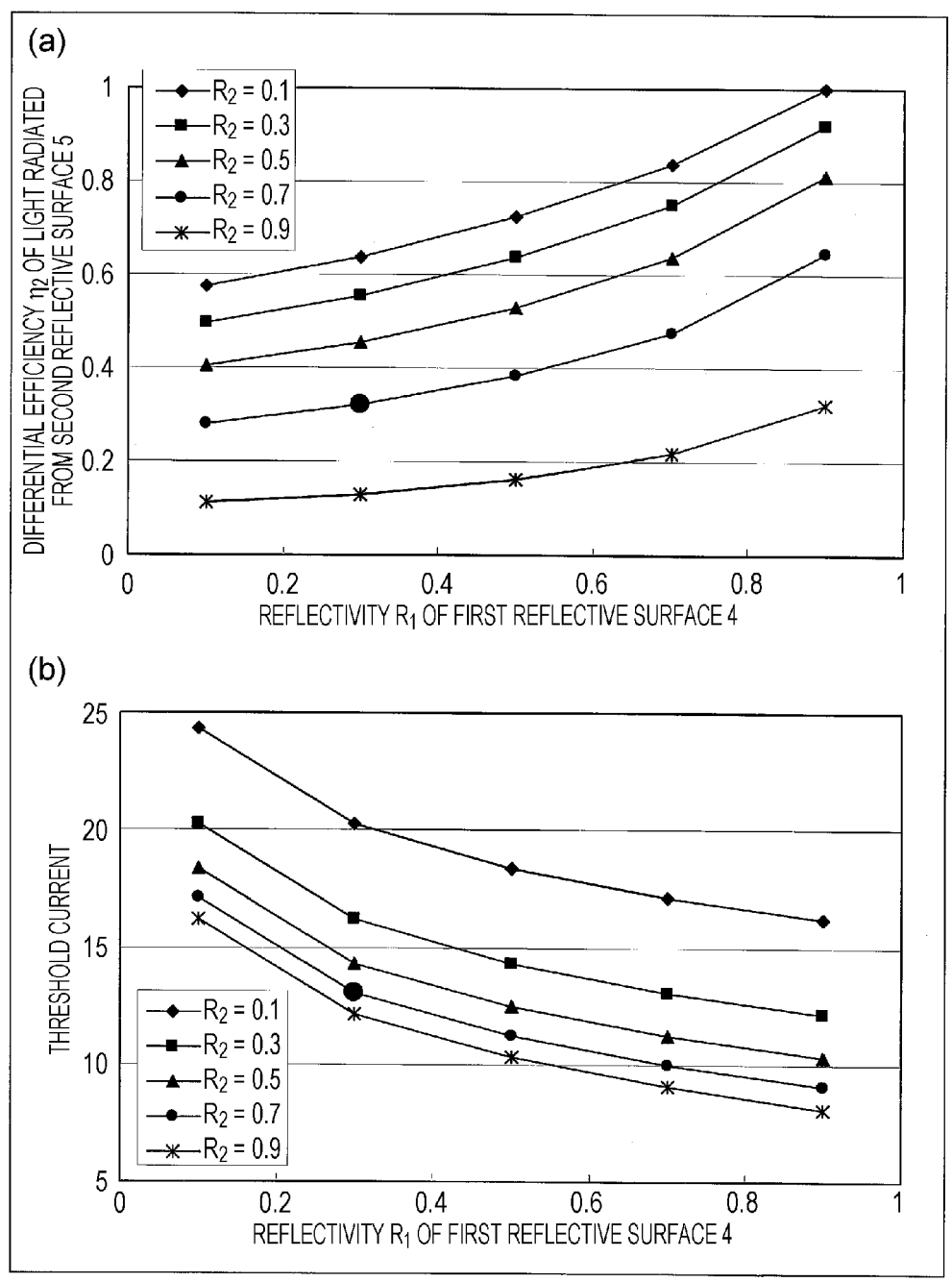
FIG. 7(a) is a graph showing the differential efficiency of light radiated from a second reflective surface when the reflectivity of a first reflective surface and the reflectivity of the second reflective surface in the optical sensor head of the optical sensor system are varied.
FIG. 7(b) is a graph showing a change in threshold current when the reflectivity of the first reflective surface and the reflectivity of the second reflective surface in the optical sensor head of the optical sensor system are varied.

FIG. 6 is a perspective view showing an example of the configuration of the optical sensor system 21 according to the first preferred embodiment of the present invention.

As shown in FIG. 6, the optical sensor system 21 includes the optical sensor head 1, details of which are illustrated in FIG. 1, a calculator circuit 51, and a display 52.

The calculator circuit 51 analyzes a result of detection by the detector 3 of the optical sensor head 1 and calculates the environmental parameter at the first reflective surface 4.

The display 52 displays a result of calculation by the calculator circuit 51. As the display 52, a commercially-available display is able to be used. The display 52 may be one which displays only a number (the environmental parameter).

If a computer is utilized as the calculator circuit 51, use of a display corresponding to the computer as the display 52 allows graphical display of the environmental parameter on the display. In the case where the computer is utilized as the calculator circuit 51, a user can enter a measurement condition and analytical content using an input device, such as a keyboard.

Note that, if a result of calculation by the calculator circuit 51 is connected to a different piece of equipment, the display 52 is unnecessary.

A program (to be described later) including an algorithm related to the operation of the optical sensor system 21 is able to be provided by a manufacturer or a distributor of the optical sensor system 21 or is able to be created by a user on the user's own.

The optical sensor system 21 is able to include a temperature sensor 14. The light-emitting device 2 generally changes in emission spectrum when temperature changes. In particular, if the light-emitting device 2 is a semiconductor laser device, an emission peak wavelength shifts to the long-wavelength side as the temperature rises. For this reason, detection of the temperature of the light-emitting device 2 by the temperature sensor 14 allows a change in a detected signal due to a wavelength shift in the light-emitting device 2 to be corrected on the basis of the temperature.

The calculator circuit 51 is able to be implemented by a logic circuit (hardware) which is formed on an integrated circuit (IC chip) or the like or is able to be implemented by software that is run or executed on a central processing unit (CPU).

In the latter case, the calculator circuit 51 includes a CPU which executes instructions of a program as a piece of software which implements functions. The calculator circuit 51 also includes a read only memory (ROM) or a storage device (such components are referred to as "recording media"), on which the program and various types of data are recorded in a form readable by a computer (or the CPU), a random access memory (RAM), onto which the program is to be loaded, and the like. The functions of various preferred embodiments of the present invention may be performed when the computer (or the CPU) reads and executes the program from the recording medium.

As the recording medium, a "non-transitory tangible medium", such as a tape, a disc, a card, a semiconductor memory, or a programmable logic circuit, can be used. The program is able to be supplied to the computer via an arbitrary transmission medium capable of transmitting the program (for example, a communication network or broadcast waves).

Note that a preferred embodiment of the present invention can also be implemented in the form of a data signal embedded in a carrier wave which is a concretization of the program through electronic transmission.

The principle of analyzing a result of detection by the detector 3 and calculating the environmental parameter, performed by the calculator circuit 51, will be described.

Note that the light-emitting device 2 is a semiconductor laser device, that a result of detection (a detected value) from the detector 3 is the intensity of light radiated from the light-emitting device 2, and that a plurality of metal microparticles 7 are formed within a range irradiated with light from the light-emitting device 2, in the description below.

As a preferred embodiment of the present invention, due to a change in environmental parameter, the refractive index of the surroundings of the metal microparticle 7 or the metal microparticle 7 itself changes, the excitation wavelength for surface plasmon excited by the metal microparticle 7 changes, and the reflectivity of the first reflective surface 4 changes. Calculation of the effect of a change in the reflectivity of the first reflective surface 4 on the oscillation condition for the semiconductor laser device as the light-emitting device 2 will be described first.

The oscillation condition for the semiconductor laser device is a combination of a threshold current and differential efficiency. The threshold current and the differential efficiency are known to be expressed by formulae (1) to (3) below.

The parameters in formulae (1) to (3) are as follows.

$\eta_1$: the differential efficiency of light radiated from the first reflective surface 4

$\eta_2$: the differential efficiency of light radiated from the second reflective surface 5

Ith: threshold current $R_1$: the reflectivity of the first reflective surface 4

$R_2$: the reflectivity of the second reflective surface 5

$T_1$: the transmittance of the first reflective surface 4

$T_2$: the transmittance of the second reflective surface 5

$\eta_{stm}$: internal differential efficiency $\eta_i$: internal quantum efficiency $\alpha_{int}$: internal loss $J_0$: transparency current $\Gamma$: the optical confinement factor of an active layer h: Planck constant v: light frequency q: electronic charge L: resonator length W: active layer width d: active layer thickness

[Formula 1]

$$\eta_1 = \eta_{sim} \frac{T_1}{2-R_1-R_2} \frac{\frac{1}{2L}\ln\frac{1}{R_1 R_2}}{\alpha_{int}+\frac{1}{2L}\ln\frac{1}{R_1 R_2}} \frac{hv}{q} \quad (1)$$

[Formula 2]

$$\eta_1 = \eta_{stm} \frac{T_2}{2-R_1-R_2} \frac{\frac{1}{2L}\ln\frac{1}{R_1 R_2}}{\alpha_{int}+\frac{1}{2L}\ln\frac{1}{R_1 R_2}} \frac{hv}{q} \quad (2)$$

[Formula 3]

$$Ith = LW \cdot \frac{d}{\eta_i \Gamma}\left(\alpha_i + \frac{1}{2L}\ln\frac{1}{R_1 R_2}\right) + J_0 \frac{d}{\eta_i} \quad (3)$$

FIG. 7(a) is a graph showing the differential efficiency $\eta_2$ of light radiated from the second reflective surface 5 when a reflectivity $R_1$ of the first reflective surface 4 and a reflectivity $R_2$ of the second reflective surface 5 in the optical sensor head 1 are varied. FIG. 7(b) is a graph showing a change in threshold current when the reflectivity $R_1$ of the first reflective surface 4 and the reflectivity $R_2$ of the second reflective surface 5 in the optical sensor head 1 are varied. For the properties shown in FIGS. 7(a) and 7(b), parameters for a typical semiconductor laser device including a wavelength of 780 nm are used.

FIG. 7(a) shows that the differential efficiency $\eta_2$ of light radiated from the second reflective surface 5 changes with a change in the reflectivity $R_1$ of the first reflective surface 4. It is also apparent that the amount of change in the differential efficiency $\eta_2$ of light radiated from the second reflective surface 5 with respect to a change in the reflectivity $R_1$ of the first reflective surface 4 increases with an increase in the reflectivity $R_1$ of the first reflective surface 4. It is further apparent that the amount of change in the differential efficiency $\eta_2$ of light radiated from the second reflective surface 5 with respect to a change in the reflectivity $R_1$ of the first reflective surface 4 increases with a decrease in the reflectivity $R_2$ of the second reflective surface 5.

Thus, to detect a refractive index from a change in the differential efficiency $\eta_2$ of light radiated from the second reflective surface 5, it is preferable that the reflectivity $R_1$ of the first reflective surface 4 be high and that the reflectivity $R_2$ of the second reflective surface 5 be low.

FIG. 7(b) shows that the threshold current changes with a change in the reflectivity $R_1$ of the first reflective surface 4. It is also apparent that the amount of change in threshold current with respect to a change in the reflectivity $R_1$ of the first reflective surface 4 increases with a decrease in the reflectivity $R_1$ of the first reflective surface 4. However, even if the reflectivity $R_2$ of the second reflective surface 5 changes, the amount of change in threshold current changes little with respect to a change in the reflectivity $R_1$ of the first reflective surface 4. That is, although the value of the threshold current increases with a decrease in the reflectivity $R_2$ of the second reflective surface 5, the slopes of all curves are almost the same, and the amount of change in threshold current changes little.

Thus, to detect a refractive index from a change in threshold current, it is preferable that the reflectivity $R_1$ of the first reflective surface 4 be low. Note that the reflectivity $R_1$ of the first reflective surface 4 being low is that the amount of light radiated from the first reflective surface 4 is large or that the amount of light absorbed at the first reflective surface 4 is large. In either case, heat is given to the detection target 9 present near the first reflective surface 4. It is thus preferable to correct a change in temperature due to the amount of heat.

If the reflectivity $R_1$ of the first reflective surface 4 changes, the intensity of light radiated from the first reflective surface 4 naturally changes. The amount of change is attributable not only to the amount of change in the reflectivity $R_1$ of the first reflective surface 4 but also to a change in the oscillation condition for the semiconductor laser device as the light-emitting device 2 due to the change in the reflectivity $R_1$ of the first reflective surface 4.

The detector 3 detects the intensity of light radiated from at least either one of the first reflective surface 4 and the second reflective surface 5. A case will be illustrated below as an example where the detector 3 detects the intensity of light radiated from the second reflective surface 5.

An emission intensity P of the semiconductor laser device is known to be expressed as a linear relation as in formula (4) below using the differential efficiency $\eta_2$ of light radiated from the second reflective surface 5 when an injection current I is not less than the threshold current Ith.

[Formula 4]

$$P=\eta_2(I-Ith) \quad (4)$$

The calculator circuit 51 is able to convert the intensity itself into an environmental parameter or is able to calculate a change in at least either one of the differential efficiency and the threshold current and convert a result of the calculation into an environmental parameter.

To obtain the differential efficiency, currents with at least two current values not less than the threshold current are fed to the light-emitting device 2 to measure the current values, and the intensities of light radiated from the second reflective surface 5 at the time of the feeding are detected by the detector 3. The calculator circuit 51 is able to obtain the differential efficiency by dividing the difference between the plurality of intensities detected by the detector 3 by the difference between the current values. As for the current values, at least two current values will do.

Note that, if the number of measurements of the current value is increased to perform fitting for detected intensities with respect to respective current values, the effect of measurement errors in a current value and a detected intensity can be reduced.

If the detector 3 is configured to detect only part of light radiated from the second reflective surface 5, the calculator circuit 51 is able to be based on a correction coefficient which is determined by the ratio between the total amount of light radiated from the second reflective surface 5 and the amount of detected light and is able to correct refractive index calculation using the predetermined correction coefficient. In this case, the calculator circuit 51 holds the correction coefficient.

In a case as well where the calculator circuit 51 calculates the threshold current, currents with at least two current values not less than the threshold current are fed, and the intensities of light radiated from the second reflective surface 5 at the time of the feeding are detected by the detector 3. The calculator circuit 51 calculates the threshold current by calculating the differential efficiency $\eta_2$ of light radiated from the second reflective surface 5 and then substituting the emission intensity at a given current value and the calculated differential efficiency $\eta_2$ into formula (4).

A method for obtaining an environmental parameter from at least either one of the threshold current and the differential efficiency will be described.

The reflectivity $R_1$ of the first reflective surface 4 is first calculated from at least either one of the threshold current and the differential efficiency. For this reason, use of at least any one of formulae (2) to (4) allows unique calculation of the reflectivity $R_1$.

To calculate the environmental parameter at the first reflective surface 4 from the calculated reflectivity $R_1$ of the first reflective surface 4, a relation between the environmental parameter at the first reflective surface 4 and the reflectivity $R_1$ of the first reflective surface 4 is obtained in advance several times by a simulation or actual measurement. A relational expression between the environmental parameter at the first reflective surface 4 and the reflectivity $R_1$ of the first reflective surface 4 is derived in advance from obtained results by, for example, fitting, such as a method of least squares, and the calculator circuit 51 is made to hold the relational expression. This allows the calculator circuit 51 to calculate the environmental parameter at the first reflective surface 4 from the reflectivity $R_1$ of the first reflective surface 4 on the basis of the relational expression.

Alternatively, it is also possible to provide an adsorption layer which adsorbs a specific molecule in the surroundings of the metal microparticle 7 in the optical sensor head 1 and detect the concentration of the specific molecule adsorbed by the adsorption layer. In this case, at least any one of the intensity of light radiated from the second reflective surface 5, the threshold current, and the differential efficiency with respect to a current value is able to be measured and recorded in advance for a sample with a known concentration, as described earlier. At least any one of the intensity of light radiated from the second reflective surface 5, the threshold current, and the differential efficiency with respect to a current value similarly obtained for a sample with an unknown concentration is compared with at least any one of the intensity of light radiated from the second reflective surface 5, the threshold current, and the differential efficiency recorded, thereby calculating the concentration. In this case, the calculator circuit 51 preferably includes a storage or memory which records a result of measuring a relation between a current value and at least any one of the intensity of light radiated from the second reflective surface 5, the threshold current, and the differential efficiency for a sample with a known concentration before the measurement. The storage or memory may be a commercially-available one, such as a hard disk, an optical disc, or a solid-state memory.

A semiconductor laser has been illustrated above as the light-emitting device. Since a change in the reflectivity of the first reflective surface 4 causes a change in the oscillation condition for the resonator, a different configuration may be adopted.

A case has been a preferred embodiment of the present invention where the detector 3 detects the intensity of light radiated from the second reflective surface 5. The same applies to a case where the detector 3 detects the intensity of light radiated from the first reflective surface 4.

EXAMPLES

Examples when the optical sensor system 21 is made to operate under different conditions will be described.

Example 1

Figure 8:
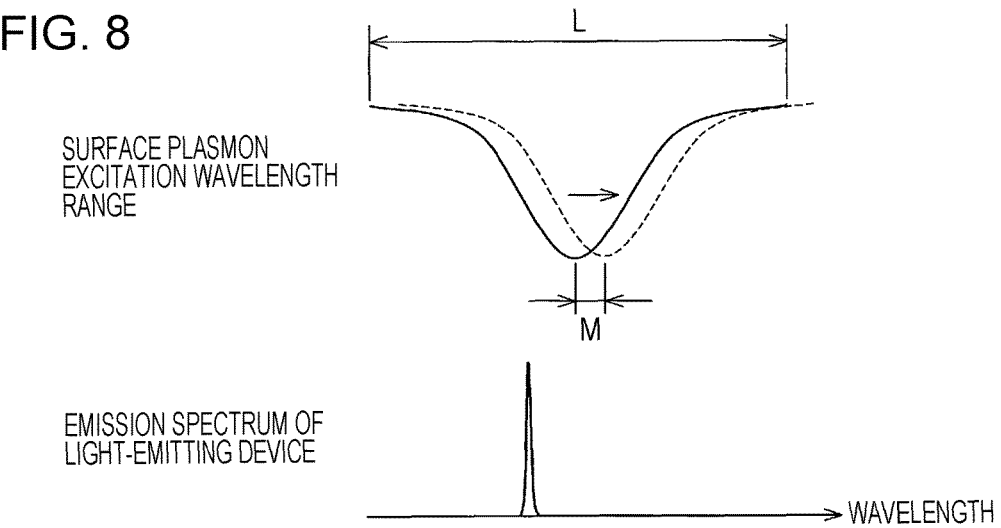
FIG. 8 is a chart showing a relation between an emission spectrum of a light-emitting device in the optical sensor system and a surface plasmon excitation wavelength range in a case where the light-emitting device oscillates in single mode.
Figure 9:
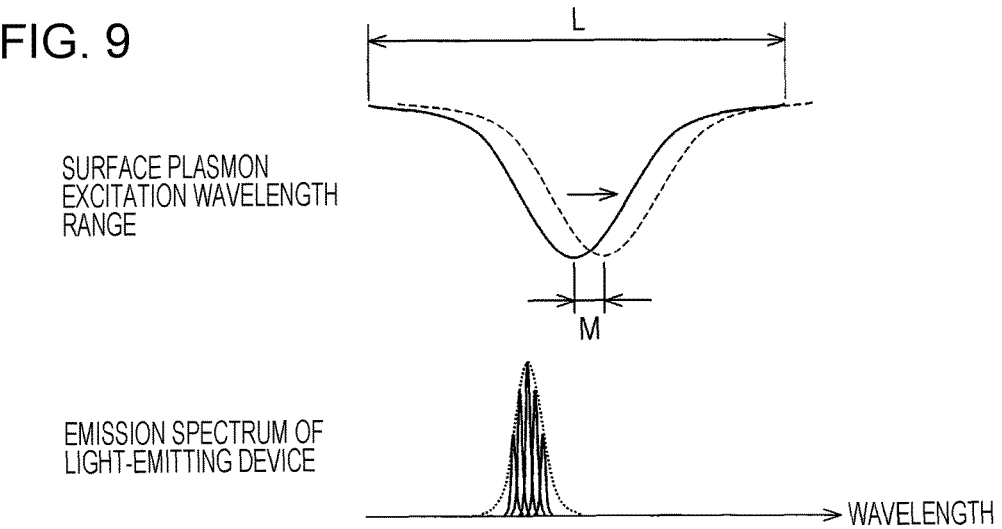
FIG. 9 is a chart showing a relation between an emission spectrum of the light-emitting device in the optical sensor system and the surface plasmon excitation wavelength range in a case where the light-emitting device oscillates in multi-mode.

FIG. 8 is a chart showing a relation between an emission spectrum of a light-emitting device 2 and a surface plasmon excitation wavelength range when the light-emitting device 2 in an optical sensor system 21 oscillates in single mode. FIG. 9 is a chart showing a relation between the emission spectrum of the light-emitting device 2 and the surface plasmon excitation wavelength range when the light-emitting device 2 in the optical sensor system 21 oscillates in multi-mode.

In Example 1 of the optical sensor system 21, a plurality of metal microparticles 7 are non-uniform in at least any one of size, aspect ratio, and alignment. More specifically, the metal microparticles 7 vary in size and aspect ratio and are not aligned in a fixed direction. With this configuration, assume that a surface plasmon excitation wavelength range L for the plurality of metal microparticles 7 is wide, and a shift amount M for (the amount of change in) a peak wavelength of the surface plasmon excitation wavelength range L due to a change in environmental parameter is less than the surface plasmon excitation wavelength range, as shown in FIG. 8.

For example, if the metal microparticles 7 are formed by sputtering or the like, the metal microparticles 7 can be made to vary both in size and aspect ratio. This allows easy fabrication of the metal microparticles 7. Additionally, it is possible to change variation ranges for size and aspect ratio and adjust the width of the surface plasmon excitation wavelength range for the metal microparticles 7 by changing a film formation condition. If a plurality of metal microparticles 7 with aspect ratios higher than 1 are dispersed without alignment, the metal microparticles 7 can be made to vary in size in a polarization direction of the light-emitting device 2.

In this state, as shown in FIG. 8, the wavelength (oscillation wavelength) of light emitted from the light-emitting device 2 is preferably not more than the peak wavelength of the surface plasmon excitation wavelength range. When a detection target 9 is mixed into gas or liquid, a refractive index generally becomes higher than that without the detection target 9, and the surface plasmon excitation wavelength range shifts to the long-wavelength side, as shown in FIG. 8. For example, assume that the graph showing the surface plasmon excitation wavelength range in FIG. 8 shows reflectivity at a first reflective surface 4. In this case, if the surface plasmon excitation wavelength range shifts to a long wavelength due to the detection target 9, reflectivity at the oscillation wavelength of the light-emitting device 2 shown in FIG. 8 monotonically increases. If the oscillation wavelength of the light-emitting device 2 is not less than the peak wavelength of the surface plasmon excitation wavelength range, when the surface plasmon excitation wavelength range shifts to a long wavelength due to the detection target 9, the reflectivity at the oscillation wavelength of the light-emitting device 2 decreases temporarily and then increases. The concentration of the detection target 9 corresponding to one reflectivity includes two values.

By setting the wavelength of light emitted from the light-emitting device 2 to be not more than the peak wavelength of the surface plasmon excitation wavelength range, when the detection target 9 is mixed into gas or liquid, the ratio of reflection from the first reflective surface 4 to light emitted from the light-emitting device 2, that is, the intensity of light radiated from the second reflective surface 5 monotonically increases or decreases. It is thus possible to detect a change in the environmental parameter at the first reflective surface 4 only from the value of or an increase or decrease in the intensity of light radiated from the second reflective surface 5. This makes the configuration of the light-emitting device 2 very simple.

Even in a case where the wavelength of light emitted from the light-emitting device 2 is more than the peak wavelength of the surface plasmon excitation wavelength range, if the wavelength is a wavelength within the surface plasmon excitation wavelength range, the ratio of reflection from the first reflective surface 4 with respect to the wavelength of light emitted from the light-emitting device 2, that is, a change in the intensity of light radiated from the second reflective surface 5 is able to be temporally recorded. This allows analysis of the environmental parameter at the first reflective surface 4. The analysis is performed by a calculator circuit 51.

Note that a case has been a preferred embodiment of the present invention where the light-emitting device 2 oscillates in single mode, as shown in FIG. 8. The same applies to a case where the light-emitting device 2 oscillates in multi-mode, as shown in FIG. 9.

Example 2

Example 2 of an optical sensor system 21 assumes that, as shown in FIG. 8 or 9, a shift amount for a peak wavelength of a surface plasmon excitation wavelength range due to a change in an environmental parameter at a first reflective surface 4 is less than the surface plasmon excitation wavelength range, like Example 1.

Note that, for expansion to the width of the surface plasmon excitation wavelength range by a plurality of metal microparticles 7, the individual metal microparticles 7 include a uniform size (particle size) not less than 100 nm and a uniform aspect ratio. The metal microparticles 7 are uniformly aligned. To obtain the configuration, for example, a plurality of metal microparticles 7 of uniform size not less than 100 nm is able to be prepared and be dispersed on the first reflective surface 4 by a silane coupling agent or the like.

If such metal microparticles 7 are used, since the metal microparticles 7 do not vary in size and aspect ratio, and the alignment lacks non-uniformity, the surface plasmon excitation wavelength range can be theoretically calculated. This allows easy analysis of a result of detection by a detector 3. If the size of the metal microparticle 7 is set to not less than 100 nm, commercially-available uniform particles is able to be uniformly dispersed on the first reflective surface 4. This allows not only easy fabrication of an optical sensor head 1 but also detection of a broad change in environmental parameter.

Example 3

Example 3 of an optical sensor system 21 assumes that, as shown in FIG. 8 or 9, a shift amount for a peak wavelength of a surface plasmon excitation wavelength range due to a change in an environmental parameter at a first reflective surface 4 is less than the surface plasmon excitation wavelength range, like Examples 1 and 2.

Note that a plurality of metal microparticles 7 include a uniform size (particle size) less than 100 nm and a uniform aspect ratio. The metal microparticles 7 are uniformly aligned.

With this configuration, the metal microparticles 7 do not vary in size and aspect ratio, and the alignment lacks non-uniformity. This allows easy analysis of a result of detection by a detector 3. Commercially-available uniform particles may be uniformly dispersed on the first reflective surface 4, which allows easy fabrication of an optical sensor head 1. Additionally, with the size less than 100 nm, the surface plasmon excitation wavelength range is narrow, and a change in environmental parameter can be detected at higher resolution accordingly.

Example 4

Figure 10:
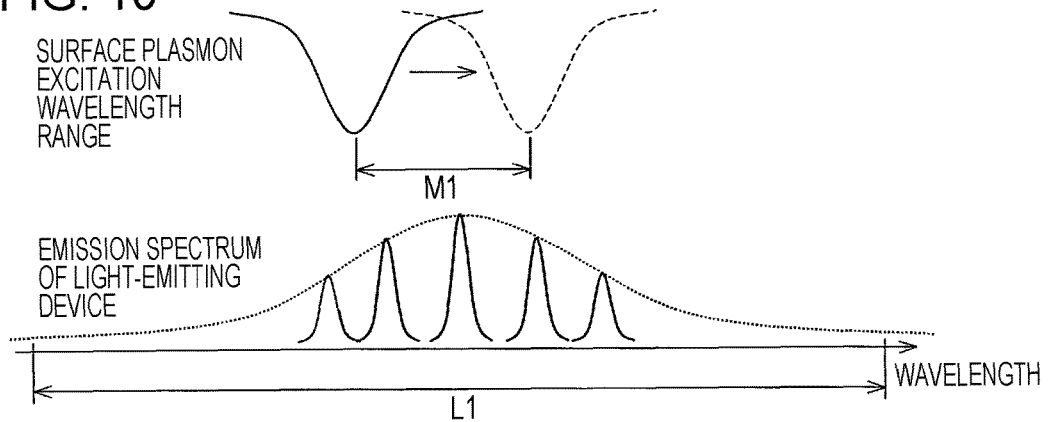
FIG. 10 is a chart showing another relation between an emission spectrum of the light-emitting device in the optical sensor system and the surface plasmon excitation wavelength range.

FIG. 10 is a chart showing another relation between the wavelength of a light-emitting device 2 in an optical sensor system 21 and a surface plasmon excitation wavelength range.

In Example 4 of the optical sensor system 21, as shown in FIG. 10, due to a change in an environmental parameter at a first reflective surface 4, a peak wavelength of a surface plasmon excitation wavelength range changes by a shift amount M1 (the amount of change). The shift amount M1 is less than a width L1 of the wavelength of light radiated from the light-emitting device 2.

As described earlier, the light-emitting device 2 generally changes in emission spectrum in response to a change in temperature. In particular, if the light-emitting device 2 is a semiconductor laser device, an emission peak wavelength shifts to the long-wavelength side as the temperature rises. Thus, the emission peak wavelength can be adjusted by changing the temperature of the light-emitting device 2. To implement this, the temperature of the light-emitting device 2 may be forcibly changed by a Peltier device or the like or light emission power of the light-emitting device 2 may be changed to cause the temperature of the light-emitting device 2 itself to change spontaneously.

Since a peak (a maximum value or a minimum value) of at least any one of the intensity of light radiated from a second reflective surface 5, a threshold current, and differential efficiency corresponds directly to the peak wavelength of the surface plasmon excitation wavelength range, the intensity of light, a threshold current, and differential efficiency for the first reflective surface 4 need not be calculated.

To calculate the environmental parameter at the first reflective surface 4 from the peak wavelength of the surface plasmon excitation wavelength range, a relation between the environmental parameter at the first reflective surface 4 and the peak wavelength of the surface plasmon excitation wavelength range is obtained in advance several times by an FDTD simulation or actual measurement, and a calculator circuit 51 is made to hold obtained results. If a relational expression between the environmental parameter at the first reflective surface 4 and the peak wavelength of the surface plasmon excitation wavelength range is derived in advance from the results by, for example, curve fitting, such as a method of least squares, the environmental parameter at the first reflective surface 4 can be calculated from the peak wavelength of the surface plasmon excitation wavelength range.

Example 5

Figure 11:
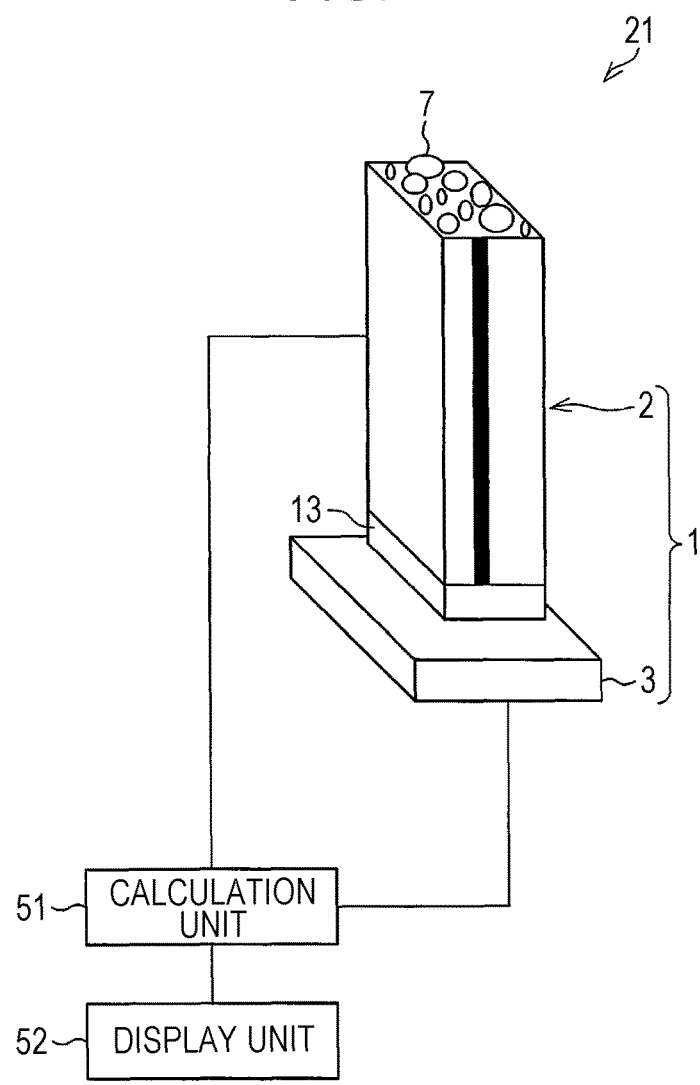
FIG. 11 is a perspective view showing another example of the configuration of the optical sensor system according to the first preferred embodiment of the present invention.

FIG. 11 is a perspective view showing an example of the configuration of an optical sensor system 21 used in Example 5.

In Example 5 of the optical sensor system 21, as shown in FIG. 10, a width L1 of the wavelength of light which can be radiated from the light-emitting device 2 is more than a shift amount M1 of a peak wavelength of a surface plasmon excitation wavelength range due to a change in an environmental parameter at a first reflective surface 4, like Example 4. As shown in FIG. 11, the optical sensor system 21 includes an external resonator 13 adjacent to the light-emitting device 2, and the light-emitting device 2 oscillates in multi-mode.

The external resonator 13 is composed of, for example, a Fabry-Perot resonator made up of two mirrors facing each other, and the interval between the mirrors are configured to be adjustable. When the mirror interval is changed, a resonant wavelength in the external resonator 13 changes, which allows change of an oscillation mode of the light-emitting device 2 from multi-mode to single mode. That is, since the surface plasmon excitation wavelength range is known from a result of detection by a detector 3 when the resonant wavelength of the external resonator 13 is changed, the environmental parameter at the first reflective surface 4 can be easily analyzed.

Second Preferred Embodiment

An optical sensor system 31 according to a second preferred embodiment of the present invention will be described with reference to FIG. 12 as follows.

Note that, in the present preferred embodiment, constituent elements including functions equivalent to those of the constituent elements in the first embodiment described earlier are denoted by identical reference numerals and that a description thereof will be omitted.

Figure 12:
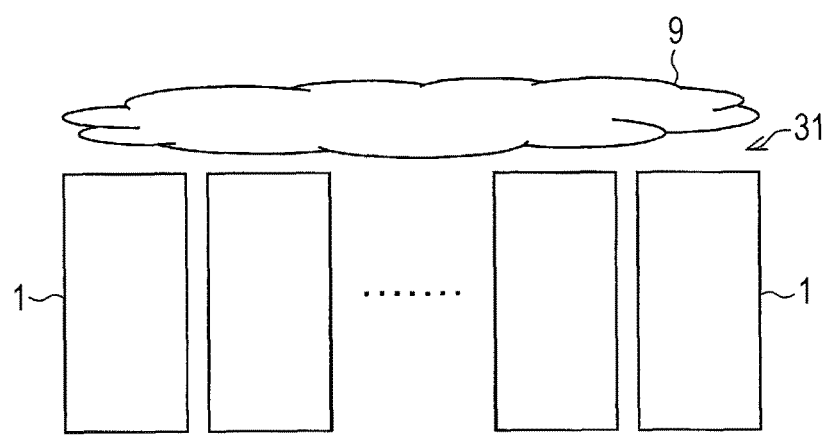
FIG. 12 is a diagram showing an example of the configuration of an optical sensor system according to a second preferred embodiment of the present invention.

FIG. 12 is a diagram showing an example of the configuration of the optical sensor system 31 according to the second preferred embodiment of the present invention.

As shown in FIG. 12, the optical sensor system 31 includes a plurality of optical sensor heads 1. In the optical sensor system 31, the number and the arrangement of the optical sensor heads 1 can be appropriately selected.

In the optical sensor system 31 with the above-described configuration, for example, if the optical sensor heads 1 are different from each other in the shape of and the material for a metal microparticle 7, and an emission wavelength of a light-emitting device 2, pieces of information obtained from the optical sensor heads 1 are different. Effects, such as more accurate detection of a detection target 9, widening of a concentration range for detection of the detection target 9, and increase of the number of types of the detection targets 9, can be obtained by putting together the pieces of information. In this case, the optical sensor heads 1 may be arranged separate from each other or be closely aligned. An arrangement interval may be set in accordance with the purpose.

Third Preferred Embodiment

An optical sensor system 32 according to a third preferred embodiment of the present invention will be described with reference to FIG. 13 as follows.

Note that, in the present preferred embodiment, constituent elements including functions equivalent to those of the constituent elements in the first and second embodiments described earlier are denoted by identical reference numerals and that a description thereof will be omitted.

Figure 13:
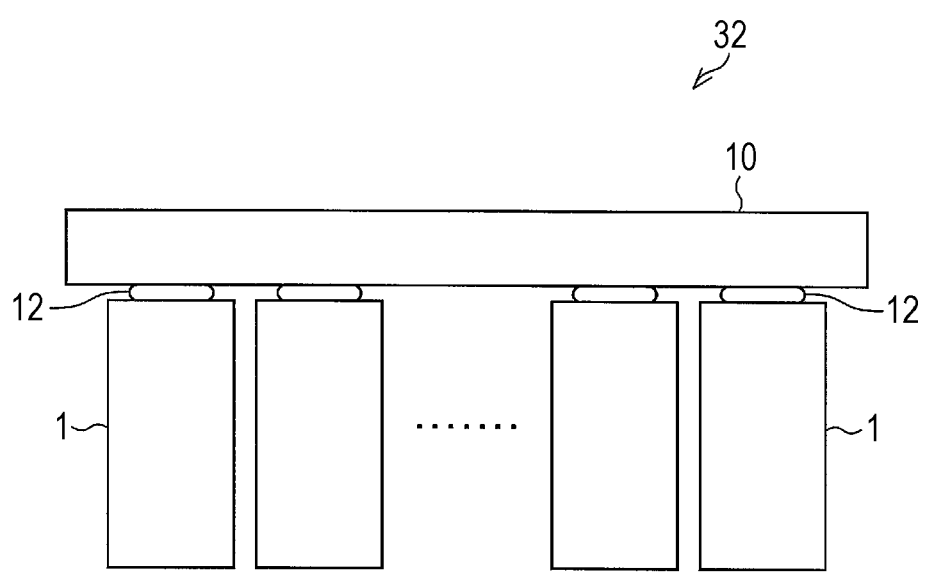
FIG. 13 is a diagram showing another example of the configuration of an optical sensor system according to a third preferred embodiment of the present invention.

FIG. 13 is a diagram showing an example of the configuration of the optical sensor system 32 according to the third preferred embodiment of the present invention.

As shown in FIG. 13, the optical sensor system 32 includes a plurality of optical sensor heads 1 including the same configuration and a flow-path member 10. The optical sensor heads 1 are aligned along the flow-path member 10. The flow-path member 10 and each optical sensor head 1 are in close contact with an O-ring 12 at facing surfaces.

In the optical sensor system 32 with the above-described configuration, a piece of time-variable or location-dependent information on a detection target 9 can be obtained by putting together pieces of information obtained from the plurality of optical sensor heads 1. Additionally, if a piece of time-variable or location-dependent information is measured while varying the temperature of the detection target 9 or the flow rate of the detection target 9, dynamic properties (for example, viscosity and the degree of dispersion) of the detection target 9 in a flow path can be known. In addition, if an adsorption layer which adsorbs a specific molecule is provided at a metal microparticle 7, and the concentration of the specific molecules is detected, a reaction condition (for example, a reaction rate or a dissociation constant) for the adsorption layer can be known.

An optical sensor system (21, 3, 321) according to a first aspect of a preferred embodiment of the present invention includes an optical sensor head (1), the optical sensor head including a light-emitting device (2) which includes a first reflective surface (4), a second reflective surface (5) facing the first reflective surface, and a waveguide (6) provided between the first reflective surface and the second reflective surface and a detector (3) which detects light emitted from the light-emitting device and including at least one metal microparticle (7) formed on the first reflective surface which excites surface plasmon, and a calculator circuit (51) which calculates an environmental parameter at the first reflective surface on a basis of a detected value from the detector.

In the configuration, the first reflective surface, the second reflective surface, and the waveguide constitute a resonator. An excitation wavelength range for surface plasmon excited at the metal microparticle is determined by the environmental parameter at the first reflective surface, and reflectivity of the first reflective surface is determined. Since an oscillation condition for the light-emitting device is determined by the reflectivity, intensity of light emitted from the light-emitting device is determined. It is thus possible to calculate the environmental parameter at the first reflective surface by the calculator circuit on a basis of intensity and a wavelength of light emitted from the light-emitting device which are detected by the detector and a parameter related to the oscillation condition, into which the intensity and wavelength are converted. It is also possible to calculate a relative change in the environmental parameter.

Since a change in intensity due to a change in oscillation condition is detected, sensitivity is higher than simple detection of a change in intensity due to a change in surface plasmon excitation wavelength range.

In an optical sensor system according to a second aspect of a preferred embodiment of the present invention, in the optical sensor system according to the first aspect, the light-emitting device may be a semiconductor laser.

In the configuration, the metal microparticle is able to be formed at a light exit surface of the semiconductor laser. The optical sensor head can be easily fabricated and is a highly-downsized, inexpensive optical sensor head. Additionally, the first reflective surface, the second reflective surface, the waveguide, and the metal microparticle can be integrally fabricated. This prevents a change over time, such as a positional shift, and enhances reliability. Since the resonator of the semiconductor laser has a gain, an S/N ratio of a detected signal can be enhanced by increasing intensity of light. Moreover, a detection result can be analyzed in more detail by detecting a change in a parameter, such as differential efficiency or a threshold current, which is the oscillation condition for the semiconductor laser.

In an optical sensor system according to a third aspect of a preferred embodiment of the present invention, in the optical sensor system according to the first aspect, the detector may be a photoelectric detector which detects light emitted from the second reflective surface in the light-emitting device and is mounted on the semiconductor laser.

A commercially-available semiconductor laser often comes with a photoelectric detector for detecting intensity of light emitted from the semiconductor laser. Utilization of the photoelectric detector as the detector allows easy fabrication of the optical sensor head.

In an optical sensor system according to a fourth aspect of a preferred embodiment of the present invention, in the optical sensor system according to the first aspect, the metal microparticle may include a shape including an aspect ratio not less than 1.

A metal material which excites surface plasmon excites surface plasmon at wavelengths from blue to green when an aspect ratio is 1. If the aspect ratio is not less than 1, a surface plasmon excitation wavelength range shifts to the long-wavelength side. Thus, an inexpensive red to infrared semiconductor laser can be used.

In an optical sensor system according to a fifth aspect of a preferred embodiment of the present invention, in the optical sensor system according to the first aspect, at least a part of the metal microparticle may be covered with a protective layer which exhibits transparency at an emission wavelength of the light-emitting device.

The configuration prevents the metal microparticle from changing over time due to a detection target or any other substance. The configuration also enhances a refractive index in surroundings of the metal microparticle and allows adjustment of a surface plasmon excitation wavelength range with respect to a wavelength of the light-emitting device.

In an optical sensor system according to a sixth aspect of a preferred embodiment of the present invention, in the optical sensor system according to the first aspect, the amount of change in a peak wavelength of a surface plasmon excitation wavelength range at the metal microparticle due to a change in the environmental parameter at the first reflective surface may be less than the surface plasmon excitation wavelength range.

In the configuration, an emission wavelength of the light-emitting device need not be changed. A change in the environmental parameter at the first reflective surface can be detected only from a change in intensity of light emitted from the light-emitting device. This allows easy construction of the optical sensor system.

In an optical sensor system according to a seventh aspect of a preferred embodiment of the present invention, in the optical sensor system according to the sixth aspect, an emission wavelength of the light-emitting device may be not more than the peak wavelength of the surface plasmon excitation wavelength range at the metal microparticle.

In the configuration, reflectivity and transmittance at the first reflective surface change monotonously with respect to a change in the environmental parameter at the first reflective surface. Since a detected value from the detector and an environmental change in surroundings of the metal microparticle correspond one-to-one to each other, analysis is easy.

In an optical sensor system according to an eighth aspect of a preferred embodiment of the present invention, in the optical sensor system according to the sixth or seventh aspect, the metal microparticle may be non-uniform in at least any one of size, aspect ratio, and alignment.

In the configuration, the surface plasmon excitation wavelength range for a plurality of metal microparticles is wide, and the amount of change in the peak wavelength of the surface plasmon excitation wavelength range due to a change in the environmental parameter at the first reflective surface can be made less than the surface plasmon excitation wavelength range. It is possible to easily fabricate the metal microparticle by forming a film of a metal material on the first reflective surface by sputtering or the like. It is also possible to change variation ranges for size and aspect ratio of the metal microparticle and adjust the surface plasmon excitation wavelength range by changing a film formation condition for the metal material.

In an optical sensor system according to a ninth aspect of a preferred embodiment of the present invention, in the optical sensor system according to the sixth aspect, the metal microparticle may include a uniform size not less than 100 nm and a uniform aspect ratio and may be uniformly aligned.

In the configuration, metal particles do not vary in size and aspect ratio, and alignment lacks non-uniformity. Thus, analysis is easy, and commercially-available uniform particles is able to be dispersed on the first reflective surface. This allows not only easy fabrication of the optical sensor system but also detection of a broad change in environmental parameter.

In an optical sensor system according to a tenth aspect of a preferred embodiment of the present invention, in the optical sensor system according to the sixth aspect, the metal microparticle may include a uniform size less than 100 nm and a uniform aspect ratio and may be uniformly aligned.

In the configuration, metal microparticles do not vary in size and aspect ratio, and alignment lacks non-uniformity. Thus, analysis is easy, and commercially-available uniform particles may be dispersed on the first reflective surface. This allows easy fabrication of the optical sensor system. At the metal microparticle with the size less than 100 nm, the surface plasmon excitation wavelength range is narrow, and a change in the environmental parameter can be detected at higher resolution accordingly.

In an optical sensor system according to an 11th aspect of a preferred embodiment of the present invention, in the optical sensor system according to the first or sixth aspect, the amount of change in the peak wavelength of the surface plasmon excitation wavelength range at the metal microparticle due to a change in an environmental parameter in surroundings of the metal microparticle may be less than a width for a wavelength of light emitted from the light-emitting device.

In the configuration, the surface plasmon excitation wavelength range can be known from a detected value from the detector when the wavelength of the light emitted from the light-emitting device is changed. This allows easy analysis of a change in the environmental parameter at the first reflective surface 4.

In an optical sensor system according to a 12th aspect of a preferred embodiment of the present invention, in the optical sensor system according to the 11th aspect, at least either one of the intensity of the light emitted from the light-emitting device and temperature of the light-emitting device may be changed.

Change of the intensity of the light emitted from the light-emitting device indirectly leads to a change in the temperature of the light-emitting device. Generally, when the light-emitting device changes in temperature, the wavelength of the light emitted from the light-emitting device changes. In the configuration, a wavelength of light that can be emitted from the light-emitting device can be easily changed only by changing either one of the intensity of the light emitted from the light-emitting device and the temperature of the light-emitting device.

In an optical sensor system according to a 13th aspect of a preferred embodiment of the present invention, in the optical sensor system according to the 11th aspect, the light-emitting device may further include an external resonator which changes in resonant wavelength.

In the configuration, when the light-emitting device is oscillating in multi-mode, an oscillation mode can be changed from multi-mode to single mode by changing the resonant wavelength of the external resonator. This allows easy change of the wavelength of the light emitted from the light-emitting device.

Various preferred embodiments of the present invention are not limited to the above-described preferred embodiments, and various changes can be made to the various preferred embodiments of the present invention. An embodiment obtained by appropriately combining technical elements or features disclosed in different preferred embodiments is included in the present invention. Additionally, a new technical feature can be achieved by combining technical elements or features disclosed in the preferred embodiments.

Various preferred embodiments of the present invention can be suitably utilized for sensing using surface plasmon resonance.

The invention claimed is:

1. An optical sensor system comprising:
an optical sensor head including:
a light-emitting device which includes a first reflective surface, a second reflective surface facing the first reflective surface, and a waveguide between the first reflective surface and the second reflective surface;
a detector which detects light emitted from the light-emitting device;
at least one metal microparticle on the first reflective surface which excites surface plasmon;
a temperature sensor that detects a temperature of the light-emitting device; and
a processor circuit including a calculator circuit which calculates an environmental parameter at the first reflective surface on a basis of a detected value from the detector and the temperature of the light-emitting device detected by the temperature sensor.

2. The optical sensor system according to claim 1, wherein a wavelength of the light emitted from the light-emitting device is changeable.

3. The optical sensor system according to claim 1, wherein at least either one of an intensity of the light emitted from the light-emitting device and a temperature of the light-emitting device is changeable.

4. The optical sensor system according to claim 1, further comprising an external resonator that is adjacent to the second reflective surface and changes in resonant wavelength by adjusting an interval between two mirrors to change an oscillation mode of the light-emitting device from multi-mode to single mode.

5. The optical sensor system according to claim 1, wherein the calculator circuit corrects a change in a detected signal due to a wavelength shift in the light-emitting device according to the temperature detected by the temperature sensor.

6. The optical sensor system according to claim 1, wherein the processor circuit adjusts an emission peak wavelength by changing the temperature of the light-emitting device.

* * * * *